United States Patent [19]

Benazzi et al.

[11] Patent Number: 6,165,439
[45] Date of Patent: *Dec. 26, 2000

[54] DEALUMINATED NU-86 ZEOLITE AND ITS USE FOR THE CONVERSION OF HYDROCARBONS

[75] Inventors: Eric Benazzi, Chatou; Nicolas Chouteau, Nanterre; Hervé Cauffriez, Bougival, all of France

[73] Assignee: Institut Francais du Petrole, Rueil Malmaison Cedex, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/974,427

[22] Filed: Nov. 19, 1997

[30] Foreign Application Priority Data

Nov. 19, 1996 [FR] France ................................ 96 14187

[51] Int. Cl.⁷ ........................ C01B 39/06; C01B 39/08; B01J 29/064; B01J 29/70
[52] U.S. Cl. ........................ 423/713; 423/714; 502/63; 502/66; 502/74; 502/85; 502/86
[58] Field of Search .................. 423/700, 713, 423/714, 715; 502/85, 86, 63, 66, 74

[56] References Cited

U.S. PATENT DOCUMENTS

| | | | |
|---|---|---|---|
| 3,506,400 | 4/1970 | Eberly, Jr. et al. | 423/713 |
| 5,043,307 | 8/1991 | Bowes et al. | 502/86 |
| 5,108,579 | 4/1992 | Casci | 208/46 |
| 5,242,676 | 9/1993 | Apelian et al. | 423/714 |
| 5,310,534 | 5/1994 | Fajula et al. | 423/714 |

FOREIGN PATENT DOCUMENTS

| | | |
|---|---|---|
| 0 095 304 | 11/1983 | European Pat. Off. . |
| 0 190 949 | 8/1986 | European Pat. Off. . |
| 0 206 871 | 12/1986 | European Pat. Off. . |
| 0 463 768 | 1/1992 | European Pat. Off. . |
| 0 564 728 | 10/1993 | European Pat. Off. . |
| 93/02994 | 2/1993 | WIPO . |

*Primary Examiner*—Mark L. Bell
*Assistant Examiner*—David Sample
*Attorney, Agent, or Firm*—Millen, White, Zelano & Branigan, P.C.

[57] ABSTRACT

The invention concerns a NU-86 zeolite comprising silicon and at least one element T selected from the group formed by aluminium, iron, gallium and boron, preferably aluminium, characterized in that element T has been extracted from the framework, and in that it has a global Si/T atomic ratio of more than about 20. Element T is extracted from the zeolitic framework (or network) by means of at least one heat treatment, optionally carried out in the presence of steam, followed by at least one acid attack using at least one solution of a mineral or organic acid, or by direct acid attack. The invention also concerns a catalyst comprising the zeolite which is at least partially in its acid form, and the use of the catalyst for the conversion of hydrocarbons, in particular for the oligomerization of olefins.

22 Claims, No Drawings

DEALUMINATED NU-86 ZEOLITE AND ITS USE FOR THE CONVERSION OF HYDROCARBONS

The invention concerns a NU-86 zeolite comprising silicon and at least one element T selected from the group formed by aluminium, iron, gallium and boron, preferably aluminium, characterized in that element T has been extracted from the framework and in that it has a global Si/T atomic ratio of more than about 20. Element T is extracted from the zeolitic framework (or network) by at least one heat treatment, optionally carried out in the presence of water, followed by at least one acid attack using at least one solution of a mineral or organic acid, or by direct acid attack. The invention also concerns a catalyst comprising the zeolite which is at least partially in its acid form. The invention further concerns the use of such a catalyst for the conversion of hydrocarbons, in particular the oligomerisation of $C_2$ to $C_8$ olefins (i.e., containing 2 to 8 carbon atoms per molecule).

The synthesis of NU-86 zeolite has been described by ICI in European patent application EP-A2-0 463 768. NU-86 zeolite is generally synthesised in the presence of sodium cations and an organic structuring agent which is either octamethonium dibromide or nonamethonium dibromide.

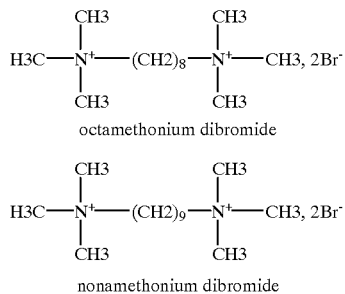

octamethonium dibromide nonamethonium dibromide

The composition of the NU-86 zeolite samples prepared have Si/Al atomic ratios in the range 8.5 to 16 and generally have Na/Al ratios of more than 8%.

The structural type of this zeolite has not yet been officially attributed by the synthesis commission of the IZA (International Zeolite Association). However, following the work published at the $9^{th}$ International Zeolite Conference by J. L Casci, P. A. Box and M. D. Shannon ("Proceedings of the $9^{th}$ International Zeolite Conference". Montreal 1992, Eds R. Von Ballmoos et al., 1993, Butterworth), it appears that:

NU-86 zeolite has a three-dimensional microporous system; the three-dimensional microporous system is constituted by
straight channels with a pore opening which is delimited by 11 T atoms (T being a tetrahedral atoms principally selected from the group formed by Si, Al, Ga and Fe), straight channels which are alternately delimited by openings with 10 and with 12 T atoms, and sinusoidal channels which are also alternately delimited by openings with 10 and with 12 T atoms.

The term "pore openings with 10, 11 or 12 tetrahedral atoms (T)" means pores constituted by 10, 11 or 12 sides. Determination of the diameter of pores present in the NU-86 zeolite have given the following values: 4.8×5.8 for pores with 10 sides, 5.7×5.7 for pores with 12 sides and 5.5×6.2 for pores with 11 sides. With these pore diameters, NU-86 zeolite belongs in the category of medium pore diameter zeolites.

The invention concerns NU-86 zeolite in which element T has been extracted from the framework by at least one heat treatment, optionally in the presence of steam, followed by at least one acid attack using at least one solution of a mineral or organic acid, or by direct acid attack using at least one solution of a mineral or organic acid, also any catalyst comprising this zeolite. The invention also concerns the use of such a catalyst for the conversion of hydrocarbons, in particular the oligomerisation of olefins.

When incorporated into a catalyst, the NU-86 zeolite (which is at least partially and preferably practically completely in its acid form and has a Si/T ratio of more than about 20), surprisingly exhibits improved catalytic performances for hydrocarbon conversion reactions over prior art catalysts, in particular as regards activities, stabilities and selectivities over the non dealuminated NU-86 zeolites described in EP-A2-0 463 768, as will be demonstrated in the Examples below.

The invention concerns a NU-86 zeolite comprising silicon and at least one element T selected from the group formed by aluminium, iron, gallium and boron, preferably aluminium, characterized in that element T has been extracted from the framework and in that it has a global Si/T atomic ratio of more than about 20, preferably more than about 22, and more preferably in the range about 22 to about 300.

The invention also concerns a catalyst comprising at least one NU-86 zeolite in which element T has been extracted from the framework and which is at least partially, preferably practically completely, in its acid form, comprising silicon and at least one element T selected from the group formed by aluminium, iron, gallium, and boron, preferably aluminium, and at least one matrix (or binder). The global atomic ratio Si/T of the dealuminated zeolite is preferably more than about 20, preferably more than about 22, and more preferably in the range about 22 to about 300. The catalyst also optionally comprises at least one element selected from the group formed by groups IB and VIII of the periodic table, preferably selected from the group formed by Ag, Ni, Pd and Pt, preferably Ni, Pd or Pt.

The matrix is generally selected from the group formed by clays (for example natural clays such as kaolin or bentonite), magnesia, aluminas, silicas, 25 titanium oxide, boron oxide, zirconia, aluminium phosphates, titanium phosphates, zirconium phosphates, silica-aluminas and charcoal, preferably from elements of the group formed by aluminas and clays.

X ray diffraction diagrams of NU-86 zeolite are given in European patent application EP-A2-0 463 768. As is well known to the skilled person, a NU-86 zeolite possesses the principal X ray diffraction peaks of its structure, but the intensity of these peaks can vary depending on the form of the zeolite, without causing any doubt that that zeolite has that structure. Thus the NU-86 zeolite in which element T has been extracted from the framework possesses the principal peaks of its structure which are given in European patent application EP-A2-0 463 768, with a peak intensity which can be different to that shown in that patent.

When it is included in the catalyst of the invention, the NU-86 zeolite of the invention is at least partially, preferably practically completely, in its acid form, i.e., in its hydrogen ($H^+$) form. The Na/T atomic ratio is generally less than 0.7%, preferably less than 0.6%, and more preferably less than 0.4%.

The catalyst of the invention generally contains 10% to 99%, preferably 20% to 95%, of NU-86 zeolite in which element T has been extracted from the framework, at least partially in its acid form. When the catalyst of the present invention contains at least one element selected from the group formed by groups IB and VIII of the periodic table, the weight content of said element(s) is generally in the range 0.01% to 10%, preferably 0.05% to 7%, more preferably 0.10% to 5%. The complement to 100% by weight generally consists of the matrix of the catalyst.

The global Si/T ratio of the zeolite and the chemical composition of the samples are determined by X ray fluorescence and atomic absorption.

For each sample, the total surface area of the signal over an angular range (2θ) of 6° to 40° is measured from the X ray diffraction diagrams, then for the same zone, the surface area of the peaks as the number of pulses for a stepwise 3 second recording with a step size of 0.02° (2θ) was measured. The ratio of these two values, surface area of peaks/ total surface area, is characteristic of the quantity of crystalline material in the sample. This ratio or "peak ratio" is then compared for each sample with the peak ratio of a reference sample which is arbitrarily considered to be completely (100%) crystalline. The degree of crystallinity is then expressed as a percentage with respect to a reference, which must be carefully selected, as the relative intensity of the peaks varies depending on the nature, the proportion and position of the different atoms in the structure unit, in particular the cations and the structuring agent. For the examples of the present description, the reference selected is the form of NU-86 which had been calcined in dry air and exchanged three times in succession with an ammonium nitrate solution.

The microporous volume can also be estimated from the quantity of nitrogen adsorbed at 77 K for a partial pressure $P/P_0$ of 0.19, for example.

The invention also concerns the preparation of the NU-86 zeolite in which element T has been extracted from the framework, and the catalyst.

The NU-86 zeolite in which element T has been extracted from the framework of the invention, in the preferred case where T is Al, i.e., the dealuminated NU-86 zeolite in the preferred case when T is Al, can be prepared by two methods from as synthesized NU-86 zeolite containing an organic structuring agent. These methods are described below. However, any other method which is known to the skilled person can also be used.

The first method, direct acid attack, comprises a first calcining step carried out in dry air, at a temperature which is generally in the range 450° C. to 550° C., which eliminates the organic structuring agent present in the micropores of the zeolite, followed by a step in which the zeolite is treated with an aqueous solution of a mineral acid such as $HNO_3$ or HCl or an organic acid such as $CH_3CO_2H$. This latter step can be repeated as many times as is necessary to obtain the desired degree of dealumination. Between these two steps, one or more ion exchange steps can be carried out using at least one $NH_4NO_3$ solution, to at least partially and preferably almost completely eliminate the alkaline cation, in particular sodium. Similarly, at the end of the direct acid attack dealumination step, one or more optional ion exchange steps can be carried out using at least one $NH_4NO_3$ solution to eliminate residual alkaline cations, in particular sodium.

In order to obtain the desired Si/Al ratio, the operating conditions must be correctly selected; the most critical parameters in this respect are the temperature of the treatment with the aqueous acid solution, the concentration of the latter, its nature, the ratio between the quantity of acid solution and the mass of the treated zeolite, the treatment period and the number of treatments carried out.

The second method, heat treatment (in particular using steam, by steaming)+acid attack, comprises firstly calcining in dry air at a temperature which is generally in the range 450° C. to 550° C., to eliminate the organic structuring agent occluded in the microporosity of the zeolite. The solid obtained then undergoes one or more ion exchanges using at least one $NH_4NO_3$ solution, to eliminate at least a portion, preferably practically all of the alkaline cation, in particular sodium, present in the cationic position of the zeolite. The zeolite obtained then undergoes at least one framework dealumination cycle comprising at least one heat treatment which is optionally and preferably carried out in the presence of steam, at a temperature which is generally in the range 550° C. to 900° C., and optionally followed by at least one acid attack using an aqueous solution of a mineral or organic acid. The conditions for calcining in the presence of steam (temperature, steam pressure and treatment period), also the post-calcining acid attack conditions (attack period, concentration of acid, nature of acid used and the ratio between the volume of the acid and the mass of zeolite) are adapted so as to obtain the desired level of dealumination. For the same reason, the number of heat treatment-acid attack cycles can be varied.

In the preferred case when T is Al, the framework dealumination cycle, comprising at least one heat treatment, step optionally and preferably carried out in the presence of steam, and at least one attack step carried out in an acid medium of the NU-86 zeolite, can be repeated as often as is necessary to obtain the dealuminated NU-86 zeolite having the desired characteristics. Similarly, following the heat treatment, optionally and preferably carried out in the presence of steam, a number of successive acid attacks can be carried out using different acid concentrations.

In a variation of this second calcining method, heat treatment of the NU-86 zeolite-containing the organic structuring agent can be carried out at a temperature which is generally in the range 550° C. to 850° C., optionally and preferably in the presence of steam. In this case, the steps of calcining the organic structuring agent and dealumination of the framework are carried out simultaneously. The zeolite is then optionally treated with at least one aqueous solution of a mineral acid (for example $HNO_3$ or HCl) or an organic acid (for example $CH_3CO_2H$). Finally, the solid obtained can optionally be subjected to at least one ion exchange step using at least one $NH_4NO_3$ solution, to eliminate practically all of the alkaline cations, in particular sodium, present in the cationic position in the zeolite.

The catalyst can be prepared using any method which is known to the skilled person. It is generally obtained by mixing the matrix and the zeolite then forming. The optional element from the group formed by groups IB and VIII of the periodic table can be introduced either before forming, or during mixing, or to the zeolite itself before mixing it or, as is preferable, after forming. Forming is generally followed by calcining, generally at a temperature which is in the range 250° C. to 600° C. The optional element from the group formed by groups IB and VIII of the periodic table can be introduced after the calcining step. In all cases, said element is generally deposited either, as is preferable, practically completely on the zeolite, or practically completely on the matrix, or partly on the zeolite and partly on the matrix, the choice depending, as will be known by the skilled person, on the parameters used during deposition, such as the nature of the precursor selected to carry out said deposition.

The element from groups IB or VIII, preferably selected from the group formed by Ag, Ni, Pd and Pt, preferably Ni, Pd or Pt, can also be deposited on the zeolite-matrix mixture prior to forming using any method which is known to the skilled person. Such deposition is generally carried out by dry impregnation, ion exchange(s) or co-precipitation. In the case of ion exchange using precursors based on silver, nickel or platinum, compounds which are normally used are silver salts such as chlorides or nitrates, a tetramine complex of platinum, or nickel salts such as chlorides, nitrates, acetates or formates. This cation exchange technique can also be used to deposit the metal directly on a zeolite powder before optional mixing with a matrix.

Optional deposition of the element(s) from groups IB and VIII is generally followed by calcining in air or oxygen, generally between 300° C. and 600° C., preferably between 350° C. and 550° C., and for a period which is in the range 0.5 to 10 hours, preferably in the range 1 to 4 hours.

When the catalyst contains several metals, these latter can be introduced either all in the same way or using different techniques, before or after forming, and in any order. When the technique used is ion exchange, several successive exchanges may be necessary to introduce the required amount of the metals.

As an example, a preferred method for the preparation of a catalyst of the invention consists of mixing the zeolite in a moist gel of the matrix (generally obtained by mixing at least one acid and a powdered matrix), for example alumina, for the period required to obtain good homogeneity of the paste obtained, i.e., about ten minutes, for example, then passing the paste through a die with a diameter in the range 0.4 to 4 mm, for example, to form extrudates. Then, after oven drying for several minutes at 100° C. and after calcining, for example for two hours at 400° C., the optional element, for example nickel, can be deposited, for example by ion exchange, deposition being followed by a final calcining step, for example for two hours at 400° C.

The catalyst of the invention is generally formed into pellets, aggregates, extrudates or spherules, depending on its use.

Catalyst preparation is generally terminated by calcining, termed final calcining, normally at a temperature which is in the range 250° C. to 600° C., preferably preceded by drying, for example oven drying, at a temperature which is generally in the range from ambient temperature to 250° C., preferably in the range 40° C. to 200° C. The exchange step is preferably carried out as the temperature is raised to carry out the calcining.

Reduction in hydrogen can then be carried out, generally at a temperature which is in the range 300° C. to 600° C., preferably in the range 350° C. to 550° C., and for a period which is in the range 1 to 10 hours, preferably in the range 2 to 5 hours, to obtain the element from groups IB and VIII mainly in the reduced form required for catalytic activity. Such a reduction can take place ex situ or in situ, with respect to the location where the catalyst is used for a given reaction.

The invention also concerns the use of the catalyst for converting hydrocarbons, in particular the oligomerisation of $C_2$ to $C_8$ olefins. In particular, the catalyst of the invention comprising dealuminated NU-86 zeolite can produce:
1) good quality premium grade gasoline;
2) excellent quality jet fuel;
3) very good quality diesel gas oil;
from light C, to $C_8$ olefins.

The starting olefins for this use can originate from any suitable source. They can also be obtained by converting methanol. Thus the following feeds can be used:
a) Fresh feed comprising mainly methanol and optionally water (in all water/methanol proportions); it is first sent to a catalytic decomposition zone where it is transformed into water and light olefins constituted principally by propene then, after separating the water formed, the light olefins are sent to an oligomerisation zone where they are transformed into a mixture of premium grade gasoline and bases for jet fuel and diesel fuel.
b) The fresh feed is constituted by light $C_2$ to $C_8$ olefins alone originating either from a catalytic cracking unit, or from a steam cracking unit, or from a catalytic dehydrogenation unit, or from any other supply source; this fresh feed is then sent directly to the oligomerisation section where it is transformed into a mixture of premium grade gasoline and bases for jet fuel and diesel fuel.
c) The fresh feed is constituted by a mixture of the two above feeds.

In the catalytic decomposition zone, the methanol is generally transformed into water and light olefins in the vapour phase in the presence of an acidic zeolitic catalyst or an acidic molecular sieve operating either in fixed bed mode or, preferably, in a fluidised catalytic system, at a temperature of about 450° C. to 650° C. (preferably between 530° C. and 590° C.) at a pressure of 0.01 to 1 MPa (preferably 0.05 to 0.5 MPa), with a liquid feed flow rate (space velocity) of about 5 to 100 volumes per volume of catalyst per hour.

The oligomerisation reaction is carried out in the liquid phase, super-critical phase or in the gaseous phase, in the presence of a fixed bed of an acidic zeolitic catalyst of the invention, at a temperature of about 50° C. to 400° C. (preferably 150° C. to 350° C.), at a pressure of 2 to 10 MPa (preferably 3 to 7 MPa), with a liquid hydrocarbon flow rate (space velocity) of about 0.3 to 4 volumes per volume of catalyst per hour.

The following examples illustrate the invention without limiting its scope.

EXAMPLE 1

Preparation of H-NU-86/1 zeolite in accordance with the invention

The starting material was a NU-86 zeolite with a global Si/Al atomic ratio of 10.2, and a sodium weight content such that the Na/Al atomic ratio was 30.8%.

This NU-86 zeolite first underwent dry calcining at 550° C. in a stream of dry air for 10 hours. The solid obtained underwent four ion exchange steps in a solution of 10 N $NH_4NO_3$ at about 100° C. for 4 hours for each exchange step. The solid obtained was designated as $NH_4$-NU-86 and had an Si/Al ratio of 10.4 and an Na/Al ratio of 1.3%. The remaining physico-chemical characteristics are shown in Table 1.

TABLE 1

| Sample | X ray diffraction Crystallinity (%) | $S_{BET}$ ($m^2$/g) | $V(P/P_0 = 0.19)$ ml liquid $N_2$/g |
|---|---|---|---|
| | | Adsorption | |
| $NH_4$NU-86 | 100 | 427 | 0.17 |

The $NH_4$-NU-86 was then hydrothermally treated in the presence of 100% of steam at 650° C., for 4 hours. The zeolite then underwent acid attack using 7 N nitric -acid at about 100° C. for 4 hours to extract the extra-framework aluminium species formed during hydrothermal treatment. The volume V of the nitric acid solution used (in ml) was 10 times the weight W of the dry NU-86 zeolite (V/W=10)

After these treatments, the H-NU-86/1 zeolite in its H form had a global Si/Al atomic ratio of 27.5 and an Na/Al ratio of less than 0.2%. These crystallographic and adsorption characteristics are shown in Table 2 below.

TABLE 2

| Sample | X ray diffraction Crystallinity (%) | Adsorption | |
|---|---|---|---|
| | | $S_{BET}$ $(m^2/g)$ | $V(P/P_0 = 0.19)$ ml liquid $N_2$/g |
| H-NU-86/1 | 100 | 426 | 0.19 |

This table shows that after the steaming and acid attack steps, the NU-86 zeolite retained good crystallinity and still had a relatively high specific surface area ($S_{BET}$).

EXAMPLE 2
Preparation of catalyst C1 in accordance with the invention

The H-NU-86/1 zeolite obtained from Example 1 was formed by extruding with an alumina gel to obtain catalyst C1, after drying and calcining in dry air, which contained 70% by weight of H-NU-86/1 zeolite and 30% of alumina.

EXAMPLE 3
Preparation of H-NU-86/2, in accordance with the invention

The starting material was the same NU-86 zeolite as that used in Example 1. Firstly this NU-86 zeolite underwent dry calcining at 550° C. in a stream of dry air for 10 hours. The solid obtained then underwent ion exchange in a 10 N $NH_4NO_3$ solution at about 100° C. for 4 hours. This operation was repeated three times in succession. The NU-86 zeolite then underwent treatment with a 0.8 N nitric acid solution at about 100° C. for 5 hours. The volume V of the nitric acid solution used (in ml) was 10 times the weight W of the dry NU-86 zeolite (V/W=10).

After these treatments, the zeolite obtained was designated as H-NU-86/2. It was in its H form and had a global Si/Al atomic ratio of 20.3 and an Na/Al ratio of 0.7%. These crystallographic and adsorption characteristics are shown in Table 3 below.

TABLE 3

| Sample | X ray diffraction Crystallinity (%) | Adsorption | |
|---|---|---|---|
| | | $S_{BET}$ $(m^2/g)$ | $V(P/P_0 = 0.19)$ ml liquid $N_2$/g |
| H-NU-86/2 | 100 | 439 | 0.18 |

EXAMPLE 4
Preparation of catalyst C2 in accordance with the invention

The H-NU-86/2 zeolite obtained from Example 3 was formed by extruding with an alumina gel to obtain catalyst C2, after drying and calcining in dry air, which contained 70% by weight of H-NU-86/2 zeolite and 30% of alumina.

EXAMPLE 5
Preparation of H-NU-86/3, in accordance with the invention

The starting material was the same NU-86 zeolite as that used in Example 1. Firstly, this NU-86 zeolite underwent dry calcining at 550° C. in a stream of dry air for 10 hours. The solid obtained then underwent ion exchange in a 10 N $NH_4NO_3$ solution at about 100° C. for 4 hours. This operation was repeated three times in succession. The NU-86 zeolite then underwent treatment with a 2 N nitric acid solution at about 100° C. for 5 hours. The volume V of the nitric acid solution used (in ml) was 10 times the weight W of the dry NU-86 zeolite (V/W=10).

After these treatments, the zeolite obtained was designated as H-NU-86/3. It was in its H form and had a global Si/Al atomic ratio of 26.2 and an Na/Al ratio of 0.6%. These crystallographic and adsorption characteristics are shown in Table 4 below.

TABLE 4

| Sample | X ray diffraction Crystallinity (%) | Adsorption | |
|---|---|---|---|
| | | $S_{BET}$ $(m^2/g)$ | $V(P/P_0 = 0.19)$ ml liquid $N_2$/g |
| H-NU-86/3 | 100 | 496 | 0.21 |

EXAMPLE 6
Preparation of H-NU-86/4, in accordance with the invention

The starting material was the same NU-86 zeolite as that used in Example 1. Firstly, this NU-86 zeolite underwent dry calcining at 550° C. in a stream of dry air for 10 hours. The solid obtained then underwent ion exchange in a 10 N $NH_4NO_3$ solution at about 100° C. for 4 hours. This operation was repeated three times in succession. The NU-86 zeolite then underwent treatment with an 8.5 N nitric acid solution at about 100° C. for 5 hours. The volume V of the nitric acid solution used (in ml) was 10 times the weight W of the dry NU-86 zeolite (V/W=10).

After these treatments, the zeolite obtained was designated as H-NU-86/4. It was in its H form and had a global Si/Al atomic ratio of 40.3 and an Na/Al ratio of 0.1–5%. These crystallographic and adsorption characteristics are shown in Table 5 below.

TABLE 5

| Sample | X ray diffraction Crystallinity (%) | Adsorption | |
|---|---|---|---|
| | | $S_{BET}$ $(m^2/g)$ | $V(P/P_0 = 0.19)$ ml liquid $N_2$/g |
| H-NU-86/4 | 98 | 469 | 0.20 |

EXAMPLE 7
Preparation of catalyst C3 in accordance with the invention

The H-NU-86/4 zeolite obtained from Example 5 was formed by extruding with an alumina gel to obtain catalyst C3, after drying and calcining in dry air, which contained 70% by weight of H-NU-86/4 zeolite and 30% of alumina.

EXAMPLE 8
Preparation of catalyst C4, not in accordance with the invention The NU-86 used in this example was the $NH_4$-NU-86 zeolite prepared in Example 1 of the present invention. However, in the present example the NU-86 zeolite did not undergo dealumination.

The H-NU-86 zeolite obtained from Example 1 was formed by extruding with an alumina gel to obtain catalyst C4, after drying and calcining in dry air, which contained 70% by weight of H-NU-86/1 zeolite and 30% of alumina.

EXAMPLE 9
Evaluation of catalytic properties for cracking methylcyclohexane using catalysts C1, C2 and C3 in accordance with the invention and catalyst C4, not in accordance with the invention Catalytic evaluations were carried out on a fixed bed at atmospheric pressure. The feed used was methylcyclohexane.

In the series of catalytic tests, the results of which are shown in Table 4, the WHSV was constant, i.e., the space velocity of the methylcyclohexane feed, (expressed as the number of grams of methylcyclohexane injected per gram of catalyst per hour) was varied so as to obtain comparable conversion in the four tests. The reaction temperature was constant at 500° C.

TABLE 6

| Catalysts | $C_1$ | $C_2$ | $C_3$ | $C_4$ |
|---|---|---|---|---|
| Methylcyclohexane conversion (wt %) | 60.1 | 60.3 | 59.8 | 60.2 |
| ($C_1 + C_2 + C_3 + C_4$) selectivity (wt %) | 63.1 | 65.3 | 67.2 | 61.9 |
| $C_5$–$C_6$ compound selectivity (wt %) | 8.9 | 9.6 | 9.1 | 9.4 |
| $C_7$ compound selectivity, isomers of methylcyclohexane (wt %) | 13.1 | 12.8 | 13.6 | 12.4 |
| (Toluene + $C_8^+$) selectivity (wt %) | 14.9 | 12.3 | 10.1 | 16.3 |

The results of Table 6 show that catalysts C1 and C3 of the invention are more effective than catalyst C4 which is not in accordance with the invention. In particular, the selectivities for products (toluene +$C_8$+), which are unwanted products which reveal the tendency of the catalyst to effect hydrogen transfer which is an unwanted reaction, are lower than for catalyst C4 which is not in accordance with the invention.

EXAMPLE 10

Evaluation of catalytic properties for oligomerisation of propylene by catalysts C1, C2, C3 of the invention, and catalyst C4 not in accordance with the invention Catalytic evaluations were carried out using a fixed bed under a pressure of 5.5 MPa of nitrogen and at 300° C. with a WHSV of 1 $h^{-1}$. The feed used was a $C_3$ steam cracking cut (5% propane, 95% propylene).

TABLE 7

| Catalysts | C1 | C2 | C3 | C4 |
|---|---|---|---|---|
| Propylene conversion | 99.8 | 99.8 | 99.8 | 99.8 |
| % gasoline cut, IP = 155° C. | 22.6 | 18.2 | 17.4 | 27.2 |
| % diesel cut > 155° C. | 77.4 | 81.8 | 82.6 | 72.8 |
| Cetane number, diesel cut | 45 | 47 | 49 | 45 |

The reaction temperature was sufficiently high (300° C.) for the variation in the Si/Al ratio of the active NU-86 phases to have no influence on the activity of catalysts C1, C2 and C3 in accordance with the invention and catalyst C4, not in accordance with the invention.

The results of Table 7 show that catalysts C1, C2 and C3 of the invention are more selective for the production of a diesel cut than catalyst C4 which is not in accordance with the invention. Increasing the selectivity for the diesel cut is accompanied by a significant increase in the cetane number for this cut.

What is claimed is:

1. A NU-86 zeolite comprising silicon and at least one element T selected from the group consisting of aluminium, iron, gallium and boron, characterized in that element T has been extracted from the framework and in that the result zeolite has a global Si/T atomic ratio of 20 to 300.

2. A zeolite according to claim 1, in which said element T is aluminium.

3. A NU-86 zeolite according to claim 2, exhibiting a crystallinity of at least about 98% by x-ray diffraction and being in the H form.

4. A NU-86 zeolite according to claim 1, comprising silicon and aluminum, characterized in that the aluminum has been extracted from the framework and in that the resultant zeolite has a global Si/Al ratio of 27.5.

5. A NU-86 zeolite according to claim 1, comprising silicon and aluminum, characterized in that the aluminum has been extracted from the framework and in that the resultant zeolite has a global Si/Al ratio of 40.3.

6. A NU-86 zeolite according to claim 1, exhibiting a crystallinity of at least about 98% by x-ray diffraction and being in the H form.

7. A process for producing a zeolite according to claim 6, comprising subjecting an NU-86 zeolite to dry calcining subjecting the resultant dry calcined solids to ion exchange steps in a solution of ammonium nitrate in order to obtain $NH_4$-NU-86; subjecting the resultant $NH_4$-NU-86 to a hydrothermal step in the presence of steam and subjecting the resultant hydrothermally treated material to acid attack with nitric acid to remove extra-framework aluminum species formed during said hydrothermal treatment.

8. A process for preparing a zeolite according to claim 1 from a synthesised NU-86 zeolite containing an organic structuring agent, said process comprising contacting said zeolite with at least one solution of a mineral or organic acid.

9. A process according to claim 8, said process further comprising a heat treatment.

10. A process according to claim 9, in which heat treatment is carried out in the presence of steam.

11. A process according to claim 9, further comprising calcining said zeolite by heating at 450° C.–900° C.

12. A process according to claim 8, further comprising calcining said zeolite by heating at 450°C.–900° C.

13. The process of claim 4, wherein said zeolite is contacted with at least one solution of a mineral acid.

14. The process of claim 4, wherein said zeolite is contacted with at least one solution of an organic acid.

15. A catalyst comprising at least one matrix and at least one zeolite in accordance with claim 1, at least partially in its acid form.

16. A catalyst according to claim 15, further comprising at least one element from groups IB or VIII of the periodic table.

17. A catalyst according to claim 16, in which said element is Ag, Ni or Pt.

18. A catalyst according to claim 15, in which the matrix is selected from the group consisting of clays, magnesia, aluminas, silicas, titanium oxide, boron oxide, zirconia, aluminium phosphates, titanium phosphates, zirconium phosphates, silica-aluminas, and charcoal.

19. A process for the preparation of a catalyst according to claim 15 comprising mixing said matrix and said zeolite, then shaping the mixture into solid bodies.

20. A zeolite according to claim 1 prepared by a process comprising contacting a synthesized NU-86 zeolite with at least one solution of a mineral or organic acid.

21. A zeolite according to claim 20, wherein said process further comprises a heat treatment.

22. A zeolite according to claim 21 wherein the heat treatment is conducted in the presence of steam.

* * * * *